US009881642B2

United States Patent
Zhang et al.

(10) Patent No.: US 9,881,642 B2
(45) Date of Patent: Jan. 30, 2018

(54) DISK SURFACE DEFECT DETECTION

(71) Applicant: Seagate Technology LLC, Cupertino, CA (US)

(72) Inventors: Lihong Zhang, Singapore (SG); Samuel Gan, Singapore (SG); Xiong Liu, Singapore (SG)

(73) Assignee: SEAGATE TECHNOLOGY LLC, Cupertino, CA (US)

( * ) Notice: Subject to any disclaimer, the term of this patent is extended or adjusted under 35 U.S.C. 154(b) by 388 days.

(21) Appl. No.: 14/674,357

(22) Filed: Mar. 31, 2015

(65) Prior Publication Data

US 2016/0293203 A1   Oct. 6, 2016

(51) Int. Cl.
*G11B 19/04* (2006.01)
*G01N 25/72* (2006.01)
*G11B 5/60* (2006.01)

(52) U.S. Cl.
CPC ............ *G11B 19/048* (2013.01); *G01N 25/72* (2013.01); *G11B 5/6052* (2013.01); *G11B 19/04* (2013.01)

(58) Field of Classification Search
CPC ..... G11B 19/048; G11B 5/6052; G11B 19/04; G01N 25/72
See application file for complete search history.

(56) References Cited

U.S. PATENT DOCUMENTS

| | | | | |
|---|---|---|---|---|
| 5,810,477 A * | 9/1998 | Abraham | ................. | G11B 5/00 374/141 |
| 6,956,707 B2 * | 10/2005 | Ottesen | ................. | G11B 5/012 360/25 |
| 8,638,349 B1 * | 1/2014 | Liu | ......... | G11B 5/607 346/78 |
| 8,737,009 B2 | 5/2014 | Kunkel et al. | | |
| 8,929,016 B2 | 1/2015 | Gao et al. | | |
| 2003/0030934 A1 * | 2/2003 | Schaff | ....................... | G11B 5/00 360/66 |
| 2003/0210488 A1 * | 11/2003 | Ottesen | ..................... | G11B 5/10 360/46 |
| 2004/0042105 A1 * | 3/2004 | Cho | ........................ | G11B 5/012 360/31 |
| 2004/0100719 A1 * | 5/2004 | Wilson | ............... | G11B 5/59633 360/75 |

(Continued)

OTHER PUBLICATIONS

Matthes, L.M, et al.; "Head-Disk Proximity Sensing Using Contact Sensors in Hard Disk Drives," Magnetics, IEEE Transactions on vol. 50, Issue 11, 2014.

(Continued)

*Primary Examiner* — Lisa Caputo
*Assistant Examiner* — Philip Cotey
(74) *Attorney, Agent, or Firm* — Holzer Patel Drennan (57) ABSTRACT

The present application provides a transducer head comprising a laser source configured to heat a target storage medium surface, and a thermal sensor configured to detect a defect on the target storage medium surface. The present application also provides a method comprising heating a target storage medium surface with an energy source configured in a transducer head to irradiate the target storage medium surface, and detecting a defect on the target storage medium surface using a thermal sensor configured in the transducer head. Other implementations are also described and recited herein.

20 Claims, 4 Drawing Sheets

(56) References Cited

U.S. PATENT DOCUMENTS

| | | | | |
|---|---|---|---|---|
| 2007/0097536 A1* | 5/2007 | Biskeborn | ............ | G11B 11/002 360/55 |
| 2011/0149706 A1* | 6/2011 | Duan | ............ | G11B 5/40 369/53.41 |
| 2012/0120519 A1* | 5/2012 | Kunkel | ............ | G11B 5/607 360/59 |
| 2012/0201108 A1* | 8/2012 | Zheng | ............ | G11B 5/607 369/13.26 |
| 2013/0163111 A1* | 6/2013 | Albrecht | ............ | G11B 5/012 360/75 |
| 2013/0286802 A1* | 10/2013 | Kiely | ............ | G11B 13/04 369/13.31 |
| 2013/0286805 A1* | 10/2013 | MacKen | ............ | G11B 5/314 369/13.33 |
| 2014/0023108 A1* | 1/2014 | Johnson | ............ | G11B 5/6076 374/45 |
| 2014/0063648 A1* | 3/2014 | Shiroishi | ............ | G11B 5/3909 360/75 |

OTHER PUBLICATIONS

Junguo Xu, et al.; Contact/Clearance Sensor for HDI Sub-nanometer Regime, IEEE Transactions on Magnetics, vol. 50 Issue 3 (1), 2014.

Xu, J, et al.; Pit Detection Using a Contact Sensor, IEEE Transactions on Magnetics, vol. 49, Issue 6 (1), 2013.

* cited by examiner

DISK SURFACE DEFECT DETECTION

BACKGROUND

In data processing systems, magnetic disk drives are used as direct access storage devices. In such devices, read/write heads are used to write data on or read data from an adjacently rotating hard or flexible disk. To prevent damage to either the disk or the read/write head, an ideal surface of the disk should be flat and free of surface defects (e.g., asperities, protrusions, voids, crevices, pits, recesses, hollows, and/or contaminated sites).

Efficient and effective systems and methods for detecting and characterizing surface defects from the storage medium surface are necessary to reduce head-medium contact events and prolong storage medium and transducer head life.

SUMMARY

Implementations described and claimed herein provide a transducer head comprising an energy source configured to heat a target storage medium surface, and a thermal sensor configured to detect a defect on the target storage medium surface. Implementations described and claimed herein also provide a method comprising heating a target storage medium surface with an energy source configured in a transducer head to irradiate the target storage medium surface, and detecting a defect on the target storage medium surface using a thermal sensor configured in the transducer head. Other implementations are also described and recited herein.

DETAILED DESCRIPTIONS

Magnetic disk surface defects (e.g., asperities, protrusions, voids, crevices, pits, recesses, hollows, and/or contaminated sites) can be detected and mapped out during media process and drive certification tests. A thermal sensor (e.g., TCR sensor, such as a differential-ended thermal coefficient of resistance (DETCR) sensor) is a built-in sensor exposed at the air-bearing surface of a head slider used for detection of defects in the storage medium. The thermal sensor can detect defects based on temperature characteristics of defects. For example, the temperature of the media surface affects the resistance of the thermal sensor and the change in the resistance of the thermal sensor is translated in dual-polarity voltage output signals generated by the thermal sensor.

However, contact defect detection methods based on a dual polarity scheme where a sensor is kept at a high temperature through a biasing voltage or current can have drawbacks. First, detection on protruding defects (e.g., thermal asperities (TAs)) is achieved through head-disk contact, in which the contact cooling and the subsequent frictional heating result in a polarized DETCR output. Therefore, the contact mode detection can cause wear and smearing on head pole areas.

Second, the detection sensitivity of a dual polarity scheme relies heavily on physical profiles of the defects. The dual polarity scheme can be inaccurate and ineffective for defects with less physical profile variations such as shallow voids or hollow-like defects. A dual polarity scheme assumes a positive polarity output of DETCR at a void defect on account of the proximity cooling when the head flies closer to the disk surface. However, the higher air-bearing pressure at proximity fly makes the sensor warmer at the same time, which acts oppositely to the proximity cooling effect to make the void detection inaccurate and ineffective, especially for shallow voids. For example, a hollow-like defect that has no abnormality on the surface is unable to be detected using the DETCR sensor alone. Ultimately, the less change of the physical profile, the lower the detection sensitivity.

Third, a dual polarity scheme operates with the DETCR sensor at high bias, wherein the sensor is heated to a temperature substantially higher than the storage medium (e.g., between about 100° C. and 300° C. higher). The sensor contacts the colder media surface and cools the sensor. The media cooling at the onset of head-medium contact generates a temperature excursion due to the sudden change in heat transfer resulting from the contact event and senses a temperature drop. Operating at a higher bias can compromise the lifespan of the thermal sensor. The temperature excursion measured by the sensor is used to detect head-medium contact.

The technology disclosed herein provides for a non-contact defect detection method comprising first heating a target storage medium surface with irradiation via a high-energy source (e.g., a laser, microwave, plasmon wave, etc.) for survey. During laser irradiation on the target surface area to be surveyed for defects, the area exposed absorbs energy from the laser source and is heated. As the local temperature in the defect increases, it measures higher than the temperature of a normal, relatively flat disk surface. The magnitude of temperature increases or decreases depending on thermal-optical properties and the surface features of the materials being irradiated. The increased or decreased temperature on the target surface area can be used as an indicator of a defect. This method negates the need for a contact thermal sensor.

After heating the survey area, defects on the target surface area are detected and mapped out on the target surface using a thermal sensor. In one implementation, the described method uses the laser of a transducer head that is used in a heat-assisted magnetic recording (HAMR) hard drive to overcome the drawbacks of contact detection in a dual polarity scheme.

For the laser of HAMR hard disk drives, the laser source can be Infrared laser or visible laser or even UV laser. The source laser propagates down a waveguide and at the end it couples with a near-field transducer (NFT) device, which then radiates into the recording medium where it is converted into thermal energy. This enables the high-energy beam to be focused on disk surface into a spot much less than the diffraction limit of the light and at the same time enhance the energy field on disk surface. The NFT feature takes different shapes for the purpose of enhancing the light field strength. For a non-HAMR laser, the waveguide and NFT may not be necessary.

The sensor (e.g., a DETCR sensor) circuit is also configured in the transducer head, located behind the laser output at the transducer area in the head, following the air-flow. For the DETCR sensor, each head has at least one DETCR sensor. Some heads may have two such sensors for each head, one for the read head and the other for the write head. DETCR is a metal wire (e.g., NiFe wire), of which the resistance changes with temperature. During defect detection and mapping, the DETCR sensor can work at DC mode as well as AC mode. Read back signals are filtered and magnified through a circuit. During defect detection and mapping, the read/write head transducers can work at passive mode (no heater power is applied to the read/write transducers) or active mode (a certain heater power is applied to make the transducer protrude to the disk surface). If some TAs are very tall (passive TAs), a DETCR sensor may still touch them during the detection/mapping even by working at passive mode.

As the transducer head travels on the media surface, the laser and the heat source are located over the target area surface first and the sensor is located over the target surface area thereafter. The disclosed method can also be used with other types of laser designs for non-HAMR drives. In other implementations, the disclosed method is used with a media multi disk-writing (MDW) process for screening media defect.

The proposed scheme can also be used to detect and map out non-intrinsic disk materials such as particles or organic contaminants on a disk surface. These materials have different thermal-optical properties from the intrinsic disk materials and their surfaces are usually much rougher than the normal disk surface. As such, their local temperature is different from the pristine disk surface under exposure of the high-energy beam. Therefore, a DETCR sensor can detect these locations.

Figure 1:
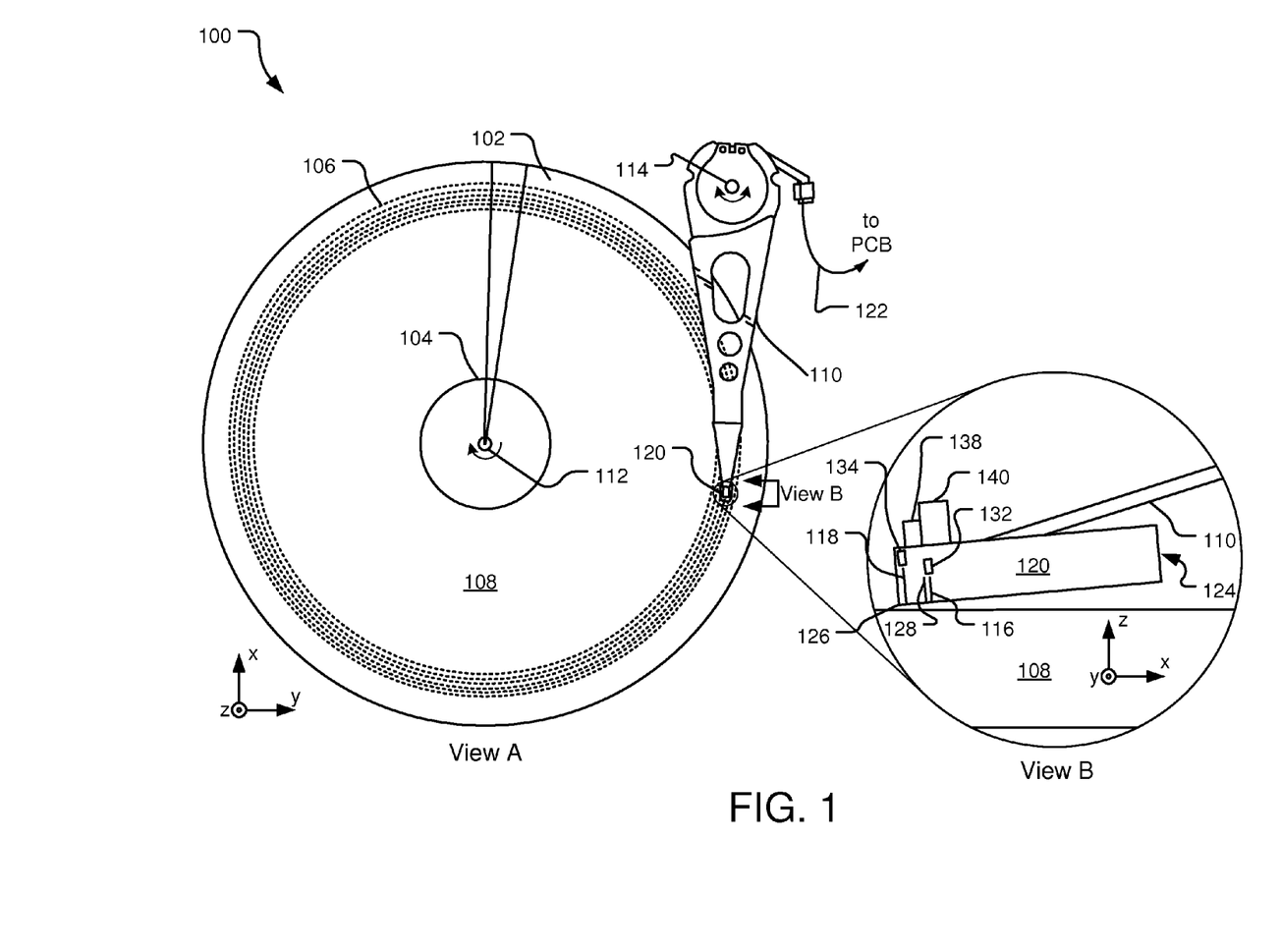
FIG. 1 illustrates an example disk drive assembly including a laser source and a thermal sensor mounted on a transducer head of a slider located at a distal end of an actuator arm and positioned over a storage medium disc.

FIG. 1 illustrates an example disk drive assembly 100 including an thermal sensor 128 and a laser source 138 configured within a slider 120 located at a distal end of an actuator arm 110 and positioned over a storage medium disk surface 108 in the disclosed technology. Referring specifically to View A (x-y plane), the disk surface 108 includes an outer diameter 102 and an inner diameter 104 between which are a number of substantially circular data tracks (e.g., track 106) illustrated by circular dotted lines. In one implementation, the disk surface 108 rotates at a high speed about disk axis of rotation 112 as information is written to and read from the data tracks on the disk surface 108. Further, the disk rotation speed may be fixed or variable.

Information may be written to and read from the disk surface 108 through the use of the actuator arm 110. The actuator arm 110 rotates about an actuator axis of rotation 114 during a seek operation to located a desired data track and sector on the disk surface 108. Specific locations on the media disk surface 108 may defined by any available addressing scheme. Example schemes include cylinder-head-sector (CHS) addressing and logical block addressing (LBA) schemes. The actuator arm 110 extends toward the disk surface 108 and the slider 120 is located at the distal end of the actuator arm 110. The slider 120 flies in close proximity above the disk surface 108 while reading and writing data to the disk surface 108. In other implementations, there is more than one slider 120, actuator arm 110, and/or disk surface 108 in the disk drive assembly 100.

A flex cable 122 provides the requisite electrical connection paths from a printed circuit board (PCB, not shown) to electronic components attached to the slider 120 (e.g., a read element 116, a write element 118, and the thermal sensor 128) while allowing pivotal movement of the actuator arm 110 during operation. The flex cable 122 may be routed along the actuator arm 110 from the PCB to the slider 120. The PCB may include circuitry (e.g., a preamplifier (pre-amp)) for controlling the write currents applied to the write element 118 during a write operation, amplifying read signals generated by the read element 116 during a read operation, and providing asperity detection using the thermal sensor 128, for example. See FIG. 2 for details regarding the preamp.

A side view of the slider 120 is shown in detail in View B of the x-z plane of FIG. 1 and includes the read element 116 and a corresponding read element heater 132, the write element 118, a corresponding write element heater 134, the laser source 138, a laser mount 140, and the thermal sensor 128, all of which are located near a trailing edge 126 of the slider 120. Other microelectronic components may also be mounted near the trailing edge 126 or on other areas of the slider 120. The appearances of the slider 120 and other features of assembly 100 are for illustration purposes only and not drawn to scale. The various microelectronic components attached to the slider 120 may be referred to in total as a transducer head 124, and are further described in detail in FIG. 2.

In this implementation, the energy source is the laser source 138, which heats the disk surface 108 for survey. During laser irradiation on the disk surface 108 to be surveyed for defects, the area exposed absorbs energy originating from the laser source 138 and is heated. As the local temperature in the defect increases, it measures higher than the temperature of a normal, relatively flat disk surface. The magnitude of temperature increases or decreases depending on thermal-optical properties and the surface features of the materials being irradiated. The increased or decreased temperature on the target surface area can be used as an indicator of a defect. This method negates the need for a contact thermal sensor. After heating the survey area, defects on the disk surface 108 are detected and mapped out on the disk surface 108 using the thermal sensor 128.

Figure 2:
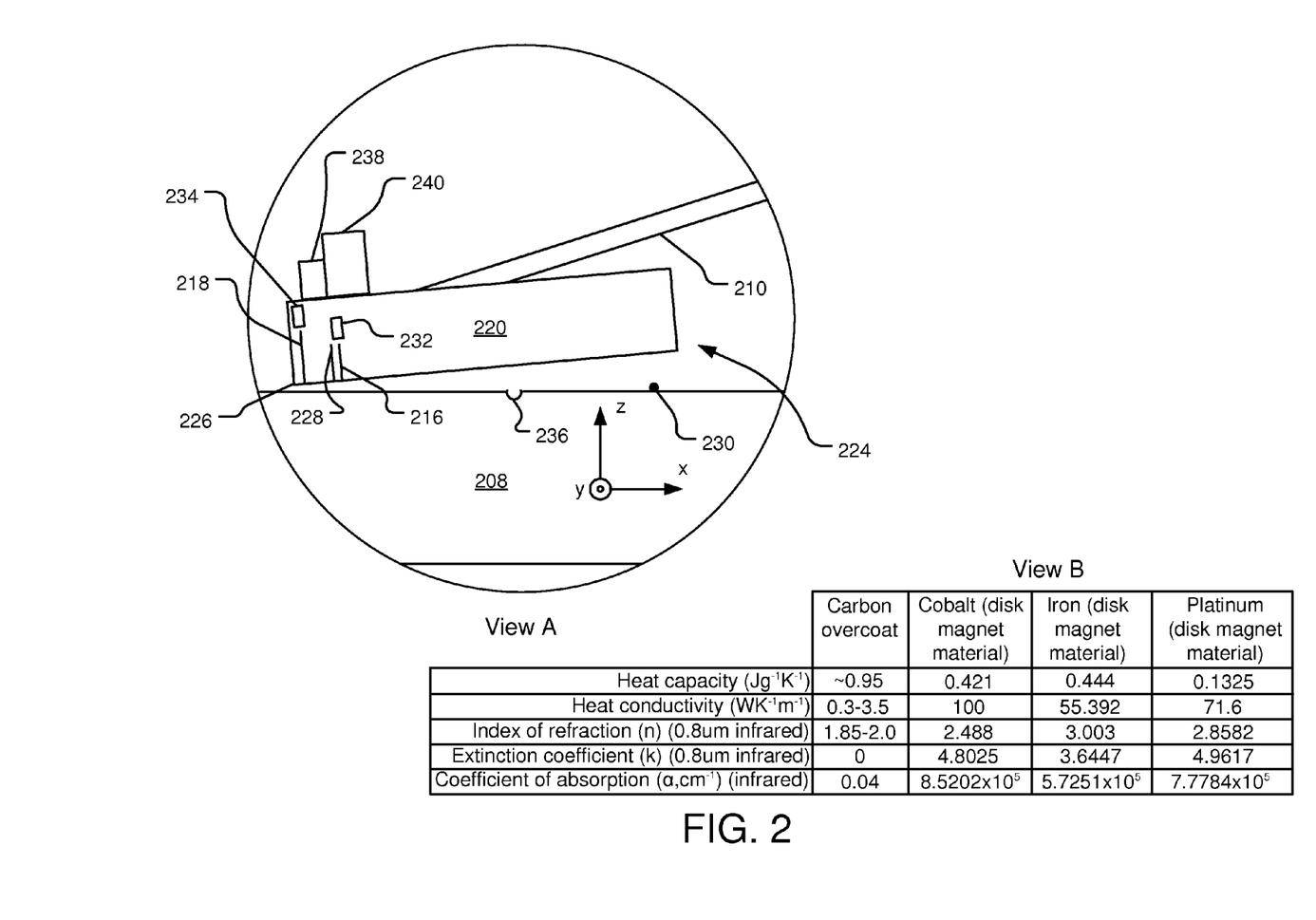
FIG. 2 illustrates an example transducer head of a slider positioned over a storage medium disk.

FIG. 2 illustrates an example transducer head of a slider positioned over a storage medium disk in View A. The side view of a slider 220 located at a distal end of an actuator arm 210 shows a read element 216, a corresponding read element heater 232, the write element 218, a corresponding write element heater 234, a laser source 238, a laser mount 240, and a thermal sensor 228, all of which are located near a trailing edge 226 of the slider 220 are shown. Other microelectronic components may also be mounted near the trailing edge 226 or on other areas of the slider 220. The appearances of the slider 220 and other features are for illustration purposes only and not drawn to scale. The various microelectronic components attached to the slider 220 may be referred to in total as a transducer head 224.

A disk surface 208 has a multitude of independent magnetic domains embedded within the disk surface 208 and the disk surface 208 generally moves in the negative x-direction with respect to the transducer head 224 in View A. The read element 216 is magnetoresistive (i.e., it has a resistance value that varies with magnetic polarity of the magnetic domains of an underlying disk as they pass underneath the read element), which allows the read element 216 to read data from the underlying disc. The write element 218 generates a magnetic field that changes the magnetic polarity of the magnetic domains of the underlying disk surface 208 as they pass underneath the write element 218. This allows the write element 218 to write data to the underlying disc.

While various efforts are made to make the disk surface 208 as smooth as possible, disk surface irregularities are inevitable at some scale. Defects are referred to herein as any variations from a substantially flat surface of the disc. These variations include thermal asperities, protrusions, voids, pits, etc. in the disk surface 208 and contaminates located on the disk surface 108. As shown in FIG. 2, the disk surface 208 has defects (e.g., void 236 or TA 230). In the disclosed technology, the disk surface 208 is heated with an energy source (e.g., laser source 238), irradiating a target surface area the disk surface 208 for survey. Then, the thermal sensor 228 detects the presence, location and scale of the defects (e.g., void 236 or TA 230) on the target surface area of the disk surface 208.

In some implementations, there may also be a waveguide and NFT (not shown) in the slider. For example, in a HAMR hard disk drive, an NFT is used to enhance the power of laser field and confine the energy beam to a spot of less 50 nm in diameter, for example. In other implementations, the waveguide and NFT may not be necessary. In one embodiment of the invention, the laser source is embedded in the slider body and its output is exposed at the slider air-bearing between the writer and reader, closer to the writer, similar to that in a HAMR head slider. For disk surface defect mapping, the laser power needed is much less than that for HAMR writing and therefore the implementation of the laser does not significantly impact the lifespan of the laser, or the workable duration of HAMR laser for write. In another embodiment of the invention, the laser device may be different from that of the HAMR laser, with a much larger high temperature spot (hot spot) size but require lower power output compared to the HAMR laser. The temperature of the hot spot can vary (e.g., 30 nm to 300 nm). The light path design is therefore much simpler than that for HAMR laser, and the laser can still fulfill its function for disk defect detection.

The magnitude of the increase in the temperature of a target surface area resulting from the laser source depends on the thermal-optical properties of the materials of the target surface area being irradiated and their surface features. Examples of such thermal optical properties of materials of a magnetic hard disk are shown in View B of FIG. 2. For example, a void on a disk surface (e.g., void 236) may be a recession without a carbon top layer. Compared to the carbon top layer (e.g., 0.95 J $g^{-1}K^{-1}$), disk magnetic materials, which are generally underneath the carbon top layer, have a much higher absorption rate to an infrared laser as well as lower heat capacities (e.g., magnetic underlayer ranging from e.g., 0.13-0.44 J $g^{-1}$ $K^{-1}$), which make the void have a much higher temperature than a pristine, flat disk surface. Moreover, the physical feature of a void can effectively trap incident light due to multiple reflections and therefore further enhance the light absorption (see below in FIG. 3B) resulting in a temperature increase. As a result, the localized temperature at a void is much higher than that of a pristine, flat site. A hot spot radiates heat, with radiation depending on the fourth power of the absolute temperature. The DETCR sensor can sense hot spots to give a positive polarity response.

For a defect such as a crevice or a pit with a carbon top layer, the localized temperature under laser irradiation can be significantly higher than a normal disk surface. This is due to the multi-scale features of the defect area that can cause significant increases in light absorption path, which leads to enhanced absorption over that of a flat smooth surface. The hot spots around the defects can be detected and mapped out by a DETCR sensor working at room temperature by giving a positive polarity output.

The disclosed technology also applies to protruding defects (e.g., TA 230). The protruding features and multi-scale texturing of a TA can reflect and scatter light back onto the surface, leading to multiple internal reflections that effectively increase the optical path length and enhance the absorption rate. As such, the temperature at a TA site is higher than the temperature of a flat, pristine surface (See FIGS. 3A and 3C).

In implementations with passive TAs, where the TAs are very tall, even at passive clearance, the head still contacts the TAs them while flying over. In such cases, no laser heat is needed as the passive TAs provides a phenomenal negative polarity response of the DETCR output.

The thermal sensor 228 is made of a material with a resistance that significantly varies with temperature (i.e., a TCR material). In various implementations, the thermal sensor 228 is made of NiFe, Ni, or Cr and has a temperature coefficient of resistance (TCR) of at least 0.002% per degree Celsius. Further, the thermal sensor 228 may be a metal wire, at least two tracks wide and large enough to provide a detectable voltage response that varies with temperature of the thermal sensor 228. Still further, the thermal sensor 228 may have a distinct material composition from the read element 216 and/or the write element 218.

Each read/write head can have one to two such sensors (e.g., a thermal sensor for the read transducer and a thermal sensor for the write transducer), however only one thermal sensor 228 is shown in FIG. 2. In an implementation with a single sensor, the sensor may be located between the read head and the write head. In an implementation with two sensors, one sensor may be located close to the read head while the other sensor may be substantially close to the write head, and either sensor can be used for defect detection on a recording medium surface. In other implementations, the sensors may be located in other areas.

Since cooling/heating effects on the transducer head 224 vary significantly depending on clearance, sudden changes in clearance (e.g., changes caused by the proximity of TA 230 to the transducer head 224) causes the thermal sensor 228 temperature to increase or decrease from a steady state operating temperature of the thermal sensor 228. Since the thermal sensor 228 has a resistance that significantly varies with temperature, a change in the resistance of the thermal sensor 228 indicates the presence and one or more spatial dimensions of a defect (e.g., TA 230).

The read element heater 232 varies a distance the read element 216 protrudes from the slider 220 toward the disk surface 208 to fine tune a clearance between the read element 216 and the disk surface 208. Similarly, the write element heater 234 varies a distance the write element 218 protrudes from the slider 120 toward the disk surface 208 to fine tune a clearance between the write element 218 and the disk surface 208. In the implementation depicted in FIG. 2, the thermal sensor 228 is located physically closer to the read element 216 and the corresponding read element heater 232 than to the write element 218 and the corresponding write element heater 234. As a result, the read element heater 232 is also used to fine-tune a clearance between the thermal sensor 228 and the disk surface 208.

In other implementations, the thermal sensor 228 may be located closer to the write element heater 234 and the write element heater 234 may be used to fine tune the clearance between the thermal sensor 228 and the disk surface 208. In yet other implementations, the thermal sensor 228 may have a dedicated heater that fine-tunes the clearance between the thermal sensor 228 and the disk surface 208. In yet other implementations, there may be no reader heater.

The technology provides for heating the disk surface 208 with constant, irradiation via a laser source (e.g., infrared laser) for survey. During laser irradiation on the disk surface 208 to be surveyed for defects, the area exposed absorbs laser light from the laser source 238 and is heated. As the local temperature in the defect increases, it measures higher than the temperature of a normal, relatively flat disk surface. The magnitude of temperature increases or decreases depending on thermal-optical properties and the surface features of the materials being irradiated. The increased or decreased temperature on the target surface area can be used as an indicator of a defect. This method negates the need for a contact thermal sensor.

After heating the survey area, defects on the target surface area are detected and mapped out on the target surface using the thermal sensor 228. In one implementation, the described method uses the laser of a transducer head that is used in a heat-assisted magnetic recording (HAMR) to overcome the drawbacks of contact detection in a dual polarity scheme. The laser 238 (e.g., an infrared laser) is a device attached to the laser mount 240, which is mounted on in the head slider 220. The sensor (e.g., a DETCR sensor) circuit is also configured in the transducer head, located behind the laser output at the transducer area in the head (not shown). It circuit output is filtered to collect the signals of interested frequency range and amplified through a preamp. Thus, as the transducer head travels on the media surface, the laser and the heat source are located over the target area surface first and the sensor is located over the target surface area thereafter.

As a result of this non-contact technology, there are several advantages. First, head and disk wear during defect detection and mapping is avoided because no head-disk contact is required with this method. Another advantage is that the disclosed technology is useful in detecting more types of defects, such as TAs, voids including shallow voids, hollow-like defects and contaminated sites, etc. Examples of these defects are shown and discussed in more detail in FIGS. 3A-3C.

Another advantage is that the DETCR sensor in this technology works at variable temperatures including room temperature at a low or minimal bias power (e.g., 50 mV-250 mV). Generally, a DETCR sensor functions by application of a higher bias with the sensor operating at higher temperatures. As a hot DETCR contacts a cold media surface, the DETCR sensor senses a temperature drop as an output. As a result of applying the higher bias, the lifespan of the DETCR sensor is adversely affected and the higher bias causes higher power consumption. However, in the disclosed technology, the DETCR sensor operates at a minimal bias, and relies on the laser for raising the temperature of the disk surface, reduces power consumption and prolongs the lifespan of the sensor.

Another advantage is that the disclosed technology can also be implemented for MDW process. The MDW process mounts a large number of disks into a spinstand and writes the servo bursts onto all of them at the same time. The disclosed technology can screen disk surface defects on a large number of disks simultaneously at a non-head-disk contact mode further reducing MDW head wear and power consumption of the process.

Yet, another advantage is that less laser power is needed from the laser source than that for HAMR writing. In yet another advantage is that the disclosed technology does not significantly affect the capability and lifespan of the laser as low laser power is needed.

The presently disclosed technology may use variable laser power and spot size of exposure on a disk for detection. Further, the disclosed technology may apply to storage drive assemblies other than the disk drive assembly 100 depicted in FIG. 1. Further yet, the presently disclosed technology may be used to detect defects on planar surfaces other than storage medium.

Figure 3A:
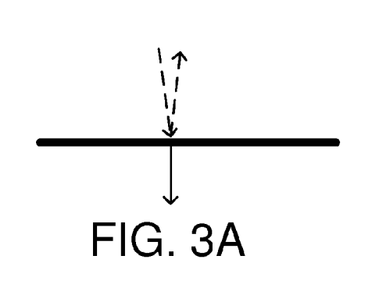
FIG. 3A illustrates a schematic diagram showing an example of a light path on a substantially flat storage medium surface.
Figure 3B:
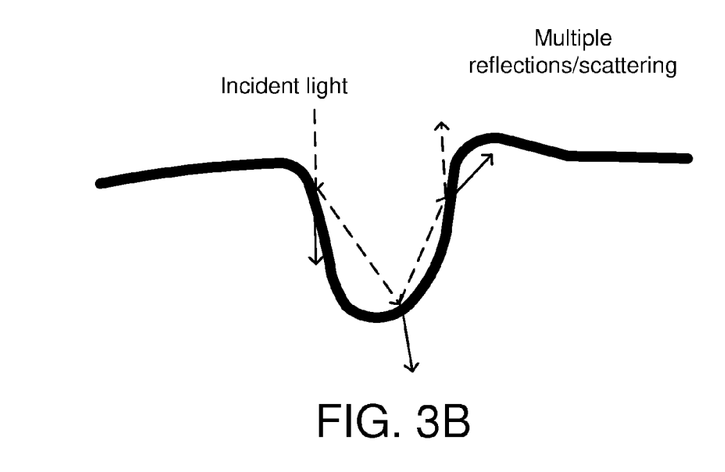
FIG. 3B illustrates a schematic diagram showing an example of a light path on a storage medium surface with a void.
Figure 3C:
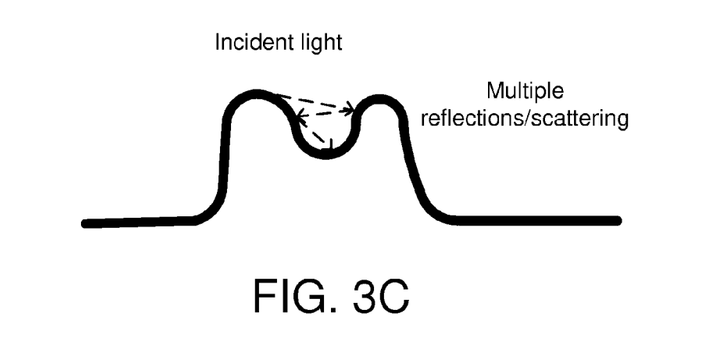
FIG. 3C illustrates a schematic diagram showing an example of a light path on a storage medium surface with thermal asperities.

FIGS. 3A-3C illustrate schematic diagrams showing examples of light paths on different disk surfaces. FIG. 3A illustrates a schematic diagram showing an example of a light path on a pristine, flat surface. The dotted lines represent the path of the incident light from a laser source to a target disk surface area and as it is reflected from the disk surface. The solid line illustrates where some of the incident light is absorbed by the disk surface. As shown, when there is a flat surface free of defect, there is a one, relatively short, reflected light path measured (see dotted line).

Compared to a normal, substantially flat or pristine disk surface a defect site, where defects have physical profile changes (and insignificant physical profile changes (e.g., hollows) due to material non-uniformity, generally has an extended light path.

FIGS. 3B and 3C illustrate examples of light reflection on surface with defects. The figures illustrate examples with voids and TAs, however, other types of defects (contaminated site and hollow defect, etc.) may be detected on the surface with the disclosed technology.

FIG. 3B illustrates a schematic diagram showing an example of light reflection on a surface with a void. As shown, there is an extended light path due to multiple light reflections on the void site. Each reflection causes more absorption by the defect and a temperature increase. The DETCR will detect the temperature increase. In an implementation with a hollow-like defect (not shown), there would be a similar extended light path with multiple reflections.

FIG. 3C illustrates a schematic diagram showing an example of light reflection on a surface with TAs. As shown, there is an extended light path due to multiple light reflections on the sites of the TAs. Similar to FIG. 3B, the defect will have a higher temperature increase than a normal, flat disk surface. The DETCR sensor detects the temperature increase.

Figure 4:
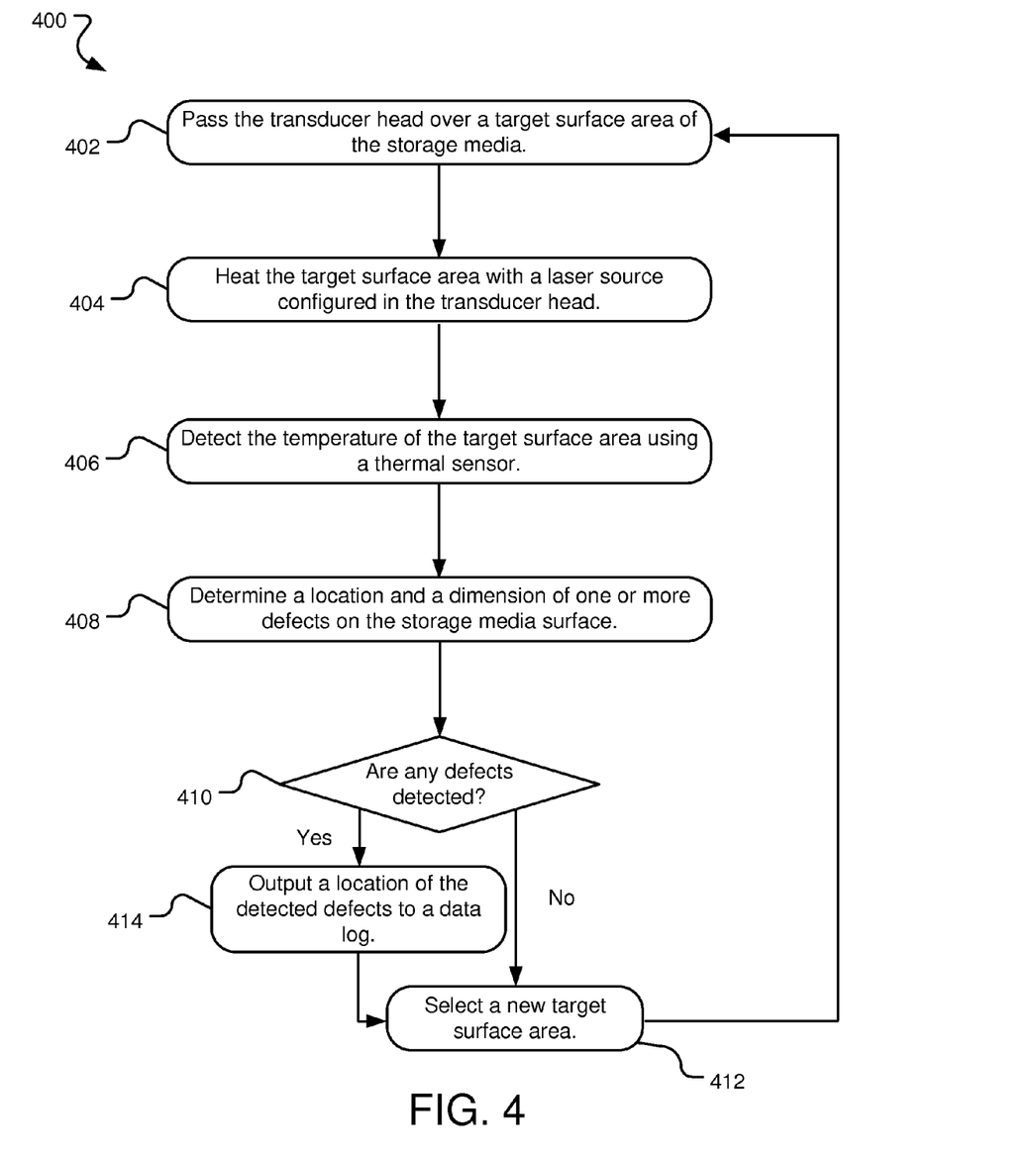
FIG. 4 illustrates example operations for detecting one or more defects on a storage medium surface.

FIG. 4 illustrates example operations 400 for detecting defects on a storage medium surface. A passing operation 402 passes a transducer head over a selected track of the storage medium. During the passing operation 402, the transducer head operates within a frequency zone associated with the selected track. In disk storage medium, the track is one of many concentric circular tracks on the storage medium. The transducer head flies in close proximity to the media surface as it passes over the selected track. The height of the transducer head as it flies above the media surface is referred to herein as clearance. In some implementations, more than one frequency zone is associated with the selected track and the passing operation 402 is performed using each frequency zone associated with the selected track.

A heating operation 404 heats a target surface area on the storage medium with a wave of high-energy beam from a high-energy source (e.g., laser, microwave, plasmon wave, etc.) configured in the transducer head. As a result, the storage medium is irradiated for survey of defects. In one implementation, the described method uses the laser of a transducer head in a heat-assisted magnetic recording (HAMR).

The localized rise in temperatures due to either profile changes or material non-uniformity, as described in FIGS. 3B-C, results in differing laser absorption. As a result, a thermal sensor (e.g., DETCR sensor) can sense defects. By inducing laser absorption, the disclosed technology is sensitive to more types of defects and can more accurately detect defects. As described above, during laser irradiation on the target surface area to be surveyed for defects, the area exposed absorbs light from the laser source and is heated, resulting in an absorption difference. The magnitude of temperature increases depending on thermal-optical properties and the surface features of the materials being irradiated.

A detecting operation 406 detects the temperature of the target surface area with the sensor. The sensor passes over the storage medium surface. The temperature change and heat transfer causes DETCR sensor resistance change, resulting in measurable DETCR sensor voltage output change. The temperature change is caused by defects on the disk surface due to unequal absorption of energy in a unit-projected area under a high-energy wave exposure (e.g., laser, microwave, plasmon wave etc.).

A voltage response is a plot of AC-coupled differential voltage across the sensor, which corresponds to temperature changes at the thermal sensor over time. More specifically, as temperature drops at the thermal sensor, the resistance of the thermal sensor drops, and thus the differential voltage across the thermal sensor increases with a negative polarity. Similarly, as the temperature rises at the thermal sensor, the resistance of the thermal sensor rises, and thus the differential voltage across the thermal sensor increases with a positive polarity.

In some implementations, the voltage response is normalized, amplified, and/or filtered to emphasize voltage changes that correspond to temperature changes at the thermal sensor over time. For example, the voltage response can be normalized to approximately 0 volts when no defects are present. In other implementations, the voltage response may be normalized to any convenient magnitude with a positive or negative polarity. A positive threshold is set (e.g., at 1 volt) and a negative threshold is set (e.g. at −1 volt) to indicate the presence of an asperity. Variations in the voltage response that do not exceed thresholds indicate baseline noise or asperities with small enough dimensions that they are ignored. The thresholds may be set at any value and may be adjusted in real time to calibrate the minimum size of detected asperities. For example, the thresholds may be set at a value that detects asperities that protrude greater than 6 nm from the storage medium surface. In one implementation, the preamp is capable of detecting voltages ranging from 1-200 mV. Thus, the thresholds may be set at magnitudes less than +200 mV and −200 mV when using such a preamp.

A determining operation 408 determines a location of defect on the irradiated storage medium surface. As the thermal sensor flies over the defect, the effective clearance between the thermal sensor and the storage medium surface increases, which decreases the speed of air or other cooling fluid flowing between the thermal sensor and the storage medium surface. The decreased cooling fluid speed decreases convective cooling of the thermal sensor, which causes a rise in the voltage response. As the thermal sensor moves away from the defect, the voltage response returns to zero or near zero. Since the magnitude of the rise in the voltage response exceeds the threshold, the defect is detected. The presence of the defect, magnitude and polarity of the voltage response, and its location on the storage medium is recorded in a table for later use.

A decision operation 410 determines if any defects are detected on the selected track. One or more voltage thresholds may be applied to a read-back voltage profile from the thermal sensor in decision operation 410. If and where the threshold(s) are exceeded, a defect is detected. If one or more defects are detected, an outputting operation 414 outputs the location of the defect to a system-level data log. For example, the outputting operation 414 may indicate one or more track sectors where a defect is detected. The outputting operation 414 may also define a location of the defect by head, track, servo wedge, and position from index. After the outputting operation 414, a selecting operation 412 selects a new target surface area.

Operations 402, 404, 406, and 408 are iteratively repeated until no defects are detected in decision operation 410. If no defects are detected in decision operation 410, passing operation 402 selects a new track in a new target surface area in selecting operation 412 and restarts performing operations 402, 404, 406, 408, and 410. Operations 400 may be repeated iteratively until all tracks are used.

Operations 400 may be performed once to map defects on the media surface in order to select or avoid regions of the media for reading/writing data and/or to set fly the height of the transducer head. In some implementation, operations 400 may be performed periodically to detect any changes in defects on the media surface.

The embodiments of the invention described herein are implemented as logical steps in one or more computer systems. The logical operations of the present invention are implemented (1) as a sequence of processor-implemented steps executing in one or more computer systems and (2) as interconnected machine or circuit modules within one or more computer systems. The implementation is a matter of choice, dependent on the performance requirements of the computer system implementing the invention. Accordingly, the logical operations making up the embodiments of the invention described herein are referred to variously as operations, steps, objects, or modules. Furthermore, it should be understood that logical operations may be performed in any order, unless explicitly claimed otherwise or a specific order is inherently necessitated by the claim language.

The above specification, examples, and data provide a complete description of the structure and use of exemplary embodiments of the invention. Since many embodiments of the invention can be made without departing from the spirit and scope of the invention, the invention resides in the claims hereinafter appended. Furthermore, structural features of the different embodiments may be combined in yet another embodiment without departing from the recited claims.

What is claimed is:

1. A transducer head comprising:
   an energy source configured to heat a target storage medium surface; and
   a thermal sensor configured to:
      measure a temperature on the heated target storage medium surface;
      detect a change in temperature across the heated target storage medium surface;
      determine whether the change in temperature measures above a predetermined threshold; and detect a defect on the target storage medium surface responsive to determining the change in temperature measures above the predetermined threshold.

2. The transducer head of claim 1, wherein the thermal sensor is a differential-ended thermal coefficient of resistance (DETCR) sensor.

3. The transducer head of claim 2, wherein the transducer head is a MDW (multiple disk writing) head and the DETCR sensor is configured to detect a defect for MDW media.

4. The transducer head of claim 2, wherein the DETCR is further configured to map the defect location.

5. The transducer head of claim 2, wherein the DETCR sensor detects the defect without contacting the target storage medium surface.

6. The transducer head of claim 1, wherein the energy source is a laser further used to provide heat-assisted magnetic recording.

7. The transducer head of claim 1, wherein the defect includes at least one of a thermal asperity, a protrusion, a void, a crevice, a hollow, a pit, a recess, and a contaminated site in the target disk surface of the storage medium.

8. The transducers head of claim 1, further comprising:
a preamplifier configured to determine the change in temperature based on a voltage response measuring above a predetermined voltage.

9. A defect detection system comprising:
a transducer head, including:
an energy source configured to heat a target storage medium surface; and
a differential-ended thermal coefficient of resistance (DETCR) sensor configured to:
measure a temperature on the heated target storage medium surface;
detect a change in temperature across the heated target storage medium surface;
determine whether the change in temperature measures above a predetermined threshold; and
detect a defect on the target storage medium surface responsive to determining the change in temperature measures above the predetermined threshold.

10. The defect detection system of claim 9, wherein the transducer head is a multiple disk write (MDW) head and the DETCR sensor is configured to detect a defect for MDW media.

11. The defect detection system of claim 9, wherein the DETCR is further configured to map the defect location.

12. The defect detection system of claim 9, wherein the DETCR sensor is configured to detects the defect without contacting the target storage medium surface.

13. The defect detection system of claim 9, wherein the energy source is a laser further used to provide heat-assisted magnetic recording.

14. The defect detection system of claim 9, wherein the energy source is a microwave.

15. A method comprising:
heating a target storage medium surface with an energy source configured in a transducer head to irradiate the target storage medium surface;
measuring a temperature on the heated target storage medium surface;
detecting a change in temperature across the heated target storage medium surface;
determining whether the change in temperature measures above a predetermined threshold; and
detecting a defect on the target storage medium surface responsive to determining the change in temperature measures above the predetermined threshold using a thermal sensor configured in the transducer head.

16. The method of claim 15, further comprising heating the target storage medium surface with a heat-assisted magnetic recording laser in the transducer head.

17. The method of claim 15, further comprising:
mapping the defect location on the target storage medium surface.

18. The method of claim 15, further comprising detecting a defect for multiple disk write media.

19. The method of claim 15, further comprising detecting a defect using a built-in differential-ended thermal coefficient of resistance (DETCR) sensor with no contact to the defect.

20. The method of claim 19, further comprising detecting a defect using a DETCR sensor without contacting the target storage medium surface.

* * * * *